（12） United States Patent
Smith et al.

(10) Patent No.: US 9,386,949 B2
(45) Date of Patent: Jul. 12, 2016

(54) DEVICE TO DETERMINE VISUO-SPATIAL ABILITY

(71) Applicant: THE UNIVERSITY OF YORK, York, Yorkshire (GB)

(72) Inventors: Stephen Smith, Heslington (GB); Michael Adam Lones, Currie (GB)

(73) Assignee: The University of York, York, Yorkshire (GB)

( * ) Notice: Subject to any disclaimer, the term of this patent is extended or adjusted under 35 U.S.C. 154(b) by 0 days.

(21) Appl. No.: 14/414,600

(22) PCT Filed: Jul. 15, 2013

(86) PCT No.: PCT/GB2013/051889
§ 371 (c)(1),
(2) Date: Jan. 13, 2015

(87) PCT Pub. No.: WO2014/009758
PCT Pub. Date: Jan. 16, 2014

(65) Prior Publication Data
US 2015/0164402 A1 Jun. 18, 2015

(30) Foreign Application Priority Data

Jul. 13, 2012 (GB) .................................. 1212553.0

(51) Int. Cl.
*A61B 5/00* (2006.01)
*A61B 5/16* (2006.01)
(Continued)

(52) U.S. Cl.
CPC ............. *A61B 5/4088* (2013.01); *A61B 5/1114* (2013.01); *A61B 5/16* (2013.01); *A61B 5/4076* (2013.01); *A61B 5/6898* (2013.01); *A61B 5/7246* (2013.01); *A61B 5/7264* (2013.01); *A61B 5/7278* (2013.01); *A61B 5/743* (2013.01);
(Continued)

(58) Field of Classification Search
CPC ....... A61B 5/11; A61B 5/1101; A61B 5/1124; A61B 5/1125
See application file for complete search history.

(56) References Cited

U.S. PATENT DOCUMENTS 9,055,904 B2 * 6/2015 Yoo ..................... A61B 3/0033

FOREIGN PATENT DOCUMENTS

WO WO 2014/009758 A1 1/2014

OTHER PUBLICATIONS

Canham et al, "Automated Scoring of a Neuropsychological Test: The Rey Osterrieth Complex Figure", Euromicro Conference, Sep. 2000, pp. 406-413, vol. 2, ISBN: 978-0-7695-0780-4, IEEE Comput., Los Alamitos, CA.
(Continued)

*Primary Examiner* — Max Hindenburg
(74) *Attorney, Agent, or Firm* — Thorpe North & Western LLP

(57) ABSTRACT

The device (10) disclosed herein assists in the diagnosis and classification of neurodegenerative diseases through the assessment of a subject's visuo-spatial ability. The device (10) has a touch-screen display (11) into which a user can input data utilizing a stylus (13) or the like. A position reader is provided, linked to a position data storage means and also a timer to link a time value to said position data, the time value being stored in a time data storage means. Storage means is also provided for preset-value data relating to known data on medical conditions, with the preset-value data having been produced in accordance with an evolutionary algorithm. A comparator compares the user input data with the preset-value data, and the result is output.

15 Claims, 1 Drawing Sheet

(51) Int. Cl.
*A61B 5/11* (2006.01)
*G09B 19/00* (2006.01)
*G06K 9/62* (2006.01)
*G06K 9/03* (2006.01)

(52) U.S. Cl.
CPC .............. *A61B 5/7475* (2013.01); *G09B 19/00* (2013.01); *A61B 5/4082* (2013.01); *G06K 9/036* (2013.01); *G06K 9/6204* (2013.01); *G06K 9/6229* (2013.01)

(56) References Cited

OTHER PUBLICATIONS

Canham et al, "Location of Structural Sections From Within a Highly Distorted Complex Line Drawing—General Articles", IEEE Proceedings: Vision, Image and Signal Processing, Dec. 2005, pp. 741-749, vol. 152, No. 6, ISSN: 1350-245X, Institution of Electrical Engineers.

Schlooz et al, "Fragmented Visuospatial Processing in Children with Pervasive Developmental Disorder", Journal of Autism and Developmental Disorders, Aug. 2006, pp. 1025-1037, vol. 36, No. 8, ISSN: 1573-3432, Kluwer Academic Publishers.

Smith et al, "Diagnosis of Parkinson's Disease Using Evolutionary Algorithms", Genetic Programming and Evolvable Machines, Oct. 2007, pp. 433-447, vol. 8, No. 4, ISSN: 1573-7632, Kluwer Academic Publishers.

Smith et al, "Implicit Context Representation Cartesian Genetic Programming for the Assessment of Visuo-Spatial Ability", Evolutionary Computation, May 2009, pp. 1072-1078, ISBN: 978-1-4244-2958-5, IEEE Congress On, Piscataway, NJ.

* cited by examiner

DEVICE TO DETERMINE VISUO-SPATIAL ABILITY

FIELD OF THE INVENTION

The present invention relates to a device to assist in determining a subject's visuo-spatial ability. The device is particularly applicable in respect of subjects having a neuro-degenerative disease such as Alzheimer's' Disease.

BACKGROUND TO THE INVENTION

A number of conditions are known which impair certain centres of the brain dealing with memory or visualisation, co-ordination, and other non-verbal functions. As examples of this are Alzheimer's, Parkinson's disease, epilepsy as well as physical trauma. Typically such impairments are predominantly in the right temporal lobe. As non-verbal impairments are often difficult to characterise, tests have been devised to assist in the assessment. Some of the tests combine assessments of motor impairment and also memory.

In the past 80 years a number of tasks have been developed many of them based around the graphic reproduction of a relatively complex 2-D line drawing: both with the original visible to the test subject and also following a timed delay after having seen the drawing. One of the central images used in this respect is the Rey-Osterrieth Complex Figure Test (ROOF). The image comprises a large number of geometrical shapes, assembled together, but without reference to any physical object with which the subject might be acquainted. There are many ways of using the ROOF test. For example, clinical experts can assess the accuracy with which lines are drawn, the relational positions and orientation of elements within the image, the speed of drawing, etc. Records of the order in which tines are drawn can be made and assessed. In addition, a subject can be provided with drawing implements of different colour and the use of these assessed.

As a variant of this, the investigator may switch the drawing implement after a preset time to determine the subject's response and how the interruption affects the ability to carry out the task.

Amongst other figure tests used, can be named the Georgian College Complex Figure Test, the Taylor Complex Figure Test etc. A relatively simple figure test, and one particularly suited to the present invention is the Benson Figure Test, as reproduced in FIG. 1.

To date the Benson Figure Test is completed on paper, possible as part of a wider series of tests. An assessment is made of the abilities of the subject in accordance with a preset list of categories and grading. Nevertheless the assessment normally needs to be made by a qualified clinician and the assessment method is relatively subjective.

It is an object of the present invention to provide a device which is usable, even by less qualified personnel to give an accurate assessment of a person's abilities and also, in certain embodiments to provide a diagnosis of the subject's condition.

SUMMARY OF THE INVENTION

According to the invention there is provided a device to be used in the assessment of a neurodegenerative condition, said device comprising:

a touch-screen display screen or digital tablet to display images or text, and to allow a user to input data;

input means, preferably in the form of a stylus enabling a user to input the data;

a position reader, linked to a position data storage means and also a timer to link a time value to said position data and time data storage means to store said time values;

preset-value data storage means in which data on medical conditions is stored, said preset-value data having been produced in accordance with an evolutionary algorithm, comparator means to compare input position data with the image or text on the screen or tablet and preset-value data;

said comparator means producing an output value and relating the output value to a medical condition.

Conveniently, the comparator means compares one of the following characteristics of the user input data and the displayed image or text:

1) measures from Gestalt psychology;
2) the accuracy with which relative positioning of pairs of shapes are positioned;
3) the precision and degree with which a shape is reproduced;
4) the similarity with which different instances of a particular shape is reproduced;
5) the extent to which a shape is dosed, e.g. of the circles or of the rectangles, triangles etc;
6) how well symmetrical shapes are reproduced such that the symmetry is maintained;
7) the existence and size of common regions between shapes;
8) the existence of incorrectly connected shapes and the degree of this incorrectness.

The device enables a rapid and accurate diagnosis of a condition to be made. Especially conveniently, measures from Gestalt Psychology are utilised.

Preferably the comparator means utilises fuzzy set operators which are of advantage in processing the data sets.

Optionally, a classifier score is ascribed to components of the input image or text to assist in their identification. The position data is conveniently vectorised to provide flexibility in processing and matching with template shapes.

The device optionally includes a processor to derive dynamic data such as velocity and acceleration data from the position data. Further optionally, said comparator compares the dynamic data with that in a dynamic data storage means.

Conveniently, the characteristics of the predefined displayed image or text are expressed as a mathematical expression, said mathematical expression having been derived utilising an evolutionary algorithm. Especially conveniently, an evolutionary evolved expression is examined to identify those common aspects of users' input data that contributed most to the expression. Further especially conveniently, a second evolutionary algorithm is derived based on the identified common aspects.

Preferably, the device derives position data at a rate of from 10-500 Hz, and especially preferably at a rate of 100-250 Hz. A value of 200 Hz is particularly preferred.

BRIEF DESCRIPTION OF THE DRAWINGS

The invention is now described with reference to the accompanying drawings which show by way of example only, one embodiment of a device. In the drawings.

DETAILED DESCRIPTION OF THE INVENTION

Figure 1:
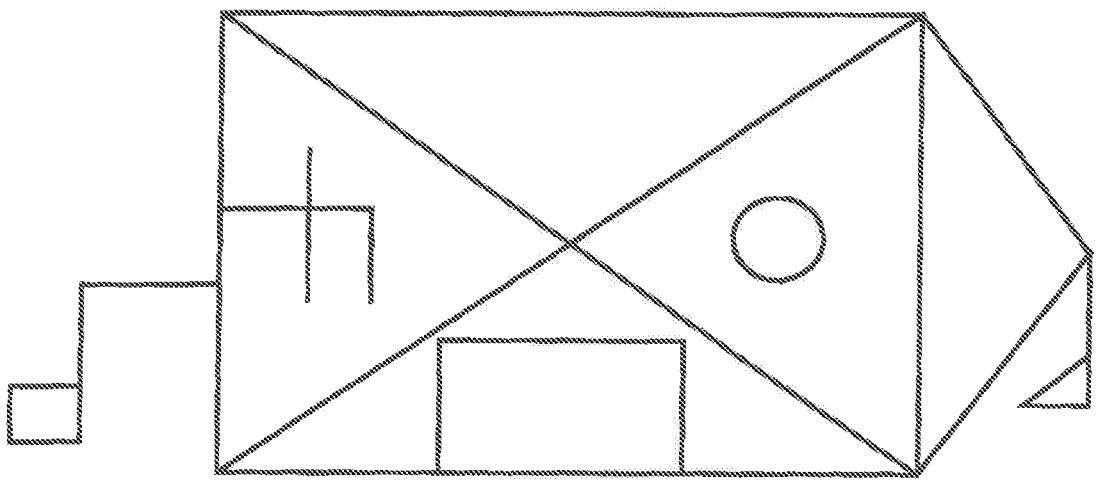
FIG. 1 shows an image forming part of a Benson Figure Test.

The assessment as to whether a subject has impairment of theft visuo-spatial abilities, the extent of any impairment which particular known condition may be giving rise to this impairment is not a simple diagnosis to make. Many conditions give rise to similar symptoms. Moreover, the subject needs to be tested in a manner which they do not perceive as threatening. The present invention discloses a relatively simple test which can produce good data to enable an accurate diagnosis to be made. The test can be carried out either at a clinic or in the subject's own premises where they feel secure.

Using the device of the present invention, the subject copies the Benson Figure which is in front of them. Normally, there is no time limit for this task, although the task is timed. As the subject carries out the task, a number of features are observed and added to a database. Typical features to be observed are:

the similarity of various shapes within the figure drawn to the original;

the accuracy of lines, the smoothness of lines, hesitancy within the drawing process etc.

As can be seen from FIG. 1, the Benson Figure is made up of a number of polygons, and the challenges for the subject are firstly to clearly reproduce the lines but also to be able to properly close the polygonal figures and to ensure that their spatial arrangement is correct. Previously, such a task was carried out on paper with the assessor then assigning marks to each aspect of this. Unfortunately, this involves a certain degree of subjectivity on behalf of the assessor in allocating the marks.

The present invention seeks to introduce more rigour into the assessment and to apply a more objective assessment of the subject's condition. Moreover, the assessment can be carried out, if desired, in the absence of a trained clinician, which reduces costs and also takes away much of the fear people often have associated with medical practitioners: so-called 'white coat syndrome'.

Figure 2:
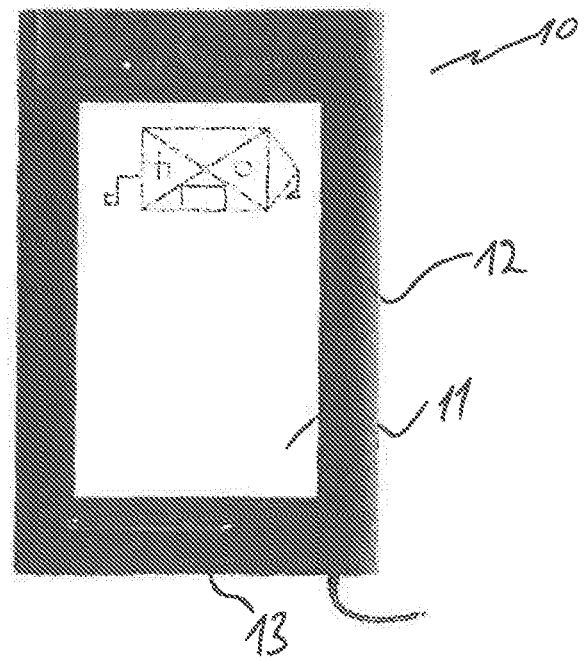
FIG. 2 is an image of a device for use in the present invention.

In FIG. 2 is shown a device 10 on which the task can be carried out. The device 10 can be battery or mains powered and has a screen 11 set in a robust surround 12. The screen 11 can display information, but can also be written or drawn on by a user using the stylus 13. One example of an apparatus which can be contemplated for use as a device of the present invention is a digitised tablet.

In use therefore, to undertake the task, the particular image to be reproduced—in this case the Benson Figure of FIG. 1 is shown in one portion of the screen 11 and the subject has to reproduce, to the best of their ability, said image in the blank screen portion, using the stylus 13.

As the subject draws the image, the device 10 samples the position and determines the orientation of the stylus 13. For example, the calculation of the orientation can be based on the previous positions visited by the stylus 13. This is carried out in the exemplified embodiment at a preferred rate of 200 Hz, although this rate can be chosen to suit the equipment and budget available and also the computing power available to process the is data produced. Typically the rate is from 10-500 Hz, although a rate of from 100-250 Hz is preferred.

The data obtained is analysed to determine a number of features. For example, abrupt changes in the stylus position and of its movement characteristics can be observed. These are often indicative of the subject leaving off drawing one sub-shape of the FIG. 1 and starting on another one. In addition, the data is vectorised and standard computer methods used to identify a particular component shape of the FIG. 1. Both of the above methods are able to segment the drawn figure into various component elements or sub-shapes.

In a final step, the results of both of the above are brought together to produce a final set of sub-shapes drawn by the subject.

Once this step has been carried out, then analysis of the correspondence of a particular sub-shape with that of that in FIG. 1 can be carried out. In addition, the spatial relationship of one sub-shape to another, including its orientation can be analysed and again compared with FIG. 1. When carrying out these analyses, then a number of characteristics, as listed below, are measured:

1) measures from Gestalt psychology;
2) the accuracy with which relative positioning of pairs of shapes are positioned;
3) the precision and degree with which a shape is reproduced;
4) the similarity with which different instances of a particular shape is reproduced;
5) the extent to which a shape is closed, e.g. of the circles or of the rectangles, triangles etc;
6) how well symmetrical shapes are reproduced such that the symmetry is maintained;
7) the existence and size of common regions between shapes;
8) the existence of incorrectly connected shapes and the degree of this incorrectness.

The results from the above analysis are stored as data sets in a form suitable for analysis, and particularly in a form suitable for analysis utilising fuzzy set operators. For example, the resulting metrics from the above analysis are given a weighting based around the process of a clinician's conventional method and then combined using a fuzzy union operator to yield a single value for grading the static properties of the image produced by the subject.

In addition to the above static properties, the dynamic aspects of the production of the image by the subject are also analysed. This can effectively be categorised into two elements: firstly, the way in which a shape is drawn in respect of movement or breaks during the observing process. Second, the movement or delay when a subject finishes one particular shape and starts on another shape.

To enable analysis to be carried out on this, classifiers are produced. The classifiers are evolved for each component shape of the Figure being drawn and also for combinations of shapes—to classify the inter-shape switch. Once the above is carried out, then the scores from each classifier can be combined to produce a single dynamical grading for the image.

Following the above steps, where static and dynamic grades have been produced, the grades are combined to give a final grading for the image.

In order to enable the categorisation of the results obtained from the above tasks, the device 10 includes data obtained from evolutionary algorithms of the type disclosed in UK patent application GB 1100794.5:

As a general description, data from a range of subjects having known conditions is assessed using the Benson Figure test, and individual movement time series are pre-processed and normalised. Evolutionary algorithms are used to devise a mathematical expression of the pattern of movement, as well as the static shapes, for the different conditions.

The evolutionary algorithm is executed a number of times. Each execution produces one or more classifiers. An ensemble classifier is then created by selecting a subset of maximally-diverse classifiers from those found during all executions of the evolutionary algorithm. This selection of maximal-diversity can be achieved either by (i) carrying out different runs of the evolutionary algorithm on different sub-sets of the data, or (ii) by post-hoc analysis, where the behaviour of each classifier is explicitly measured and those with minimal behavioural overlap are chosen for the ensemble. Behaviour, in this sense, can either be the differential response of the classifier to different subsets of the data, or the classifier's ability to recognise particular patterns within the data.

The mathematical expression is then used to classify data obtained from new subjects and to determine the condition, if any, suffered by the subject. In a further aspect of the invention, expressions can be included which enable the prediction of cognitive skills such as executive function, spatial perception, memory etc. Additionally, motor skills (such as bradykinesia, tremor types) or disease-related MRI markers (such as hippocampal or parietal volume) can be categorised.

In a preferred embodiment therefore, the subject's drawings are firstly digitized using a computer graphics tablet, or similar device. Particular candidate shapes are located within a graph representation of the pre-processed line drawings, and these candidates shapes are rated. The rating is in accordance with a set of fuzzy rules based upon Gestalt principles of human visual perception. The shapes with the highest rating, that relate to shapes in the Benson Test (or other conventional scheme) are marked in a conventional manner by specialists in this field. The candidate shapes together with the specialist's marks are used to train a separate evolutionary algorithm to arrive at the same result for each shape in the conventional marking scheme. The resulting set of evolutionary algorithms, one for each shape in the marking scheme, are then used to automatically and objectively assess the new subject's drawings.

In more general terms, once an evolutionary algorithm has been trained for a particular shape, in the conventional marking scheme, the evolved expression is examined to identify those common aspects of all subjects' drawing activities that contributed most to the expression. Using those specific aspects alone, a second evolutionary algorithm is trained to evolve a better, more discriminating expression.

In drawing up the above categories the variables taken into account by the algorithms, include velocity and acceleration data generated from the position data of the stylus on the screen, the order in which elements are drawn, which provides information on the sequencing and memory skills of the subject. Also, the spatial positioning and properties of the elements along with frequency of tremor displayed by the subject is also included.

The invention claimed is:

1. A device for use in the assessment of a neurodegenerative condition, said device comprising:
   a touch-screen display screen or digital tablet to display predefined images or text, and to allow a user to input data;
   a stylus enabling a user to input the data;
   a position reader, linked to a position data storage and also a timer to link a time value to said position data and time data storage to store said time values;
   preset-value data storage in which data on medical conditions is stored, said preset-value data storage having been produced in accordance with an evolutionary algorithm; and
   a comparator to compare input position data with the predefined image or text on the screen or tablet and preset-value data;
   said comparator producing an output value and relating the output value to a medical condition.

2. A device according to claim 1, wherein the comparator compares one of the following characteristics of the input data and the predefined image or text:
   1) measures from Gestalt psychology;
   2) the accuracy with which relative positioning of pairs of shapes are positioned;
   3) the precision and degree with which a shape is reproduced;
   4) the similarity with which different instances of a particular shape is reproduced;
   5) the extent to which a shape is closed, e.g. of the circles or of the rectangles, triangles etc;
   6) how well symmetrical shapes are reproduced such that the symmetry is maintained;
   7) the existence and size of common regions between shapes; and
   8) the existence of incorrectly connected shapes and the degree of this incorrectness.

3. A device according to claim 2, wherein measures from Gestalt Psychology are used.

4. A device according to claim 2, wherein said comparator utilises fuzzy set operators.

5. A device according to claim 2, wherein a classifier score is ascribed to components of the predefined image or text.

6. A device according to claim 1, wherein the position data is vectorised.

7. A device according to claim 1, wherein the device includes a processor to derive dynamic data such as velocity and acceleration data from the position data.

8. A device according to claim 7, wherein said comparator compares the dynamic data with that in a dynamic data storage.

9. A device according to claim 7, wherein the input data and dynamic data are assigned classification values.

10. A device according to claim 1, wherein the characteristics of the predefined image or text are expressed as a mathematical expression, said mathematical expression having been derived utilising an evolutionary algorithm.

11. A device according to claim 10, wherein an evolutionary evolved expression is examined to identify those common aspects of users' input data that contributed most to the expression.

12. A device according to claim 11, wherein a second evolutionary algorithm is derived based on the identified common aspects.

13. A device according to claim 1, wherein the device derives position data at a rate of from 10-500 Hz.

14. A device according to claim 1, wherein the position data is derived at a rate of 100-250 Hz.

15. A device according to claim 1, wherein the position data is derived at a rate of 200 Hz.

* * * * *